United States Patent [19]

DiSalvo et al.

[11] 4,195,634

[45] Apr. 1, 1980

[54] SANITARY NAPKIN WITH RESILIENT STIFFENING MEANS

[75] Inventors: Walter A. DiSalvo, North Arlington; Robert B. Cubitt, Saddle Brook; Francis J. Coury, Highland Park, all of N.J.

[73] Assignee: International Playtex, Inc., Stamford, Conn.

[21] Appl. No.: 921,654

[22] Filed: Jul. 3, 1978

[51] Int. Cl.² .................................. A61F 13/116
[52] U.S. Cl. ................ 128/290 R; 128/DIG. 30
[58] Field of Search ............ 128/288, 285, 286, 287, 128/290 R, 290 W, 290 P, 296, DIG. 30

[56] References Cited

U.S. PATENT DOCUMENTS

| 3,651,809 | 3/1972 | Champaigne, Jr. | 128/290 R |
| 3,688,771 | 9/1972 | Werner | 128/290 R |
| 3,724,466 | 4/1973 | Hendricks | 128/290 R |
| 3,858,585 | 1/1975 | Chatterjee | 128/290 R |
| 3,897,783 | 8/1975 | Ginocchio | 128/290 R |
| 3,986,511 | 10/1976 | Olofsson et al. | 128/285 |

Primary Examiner—Robert W. Michell
Assistant Examiner—C. F. Rosenbaum
Attorney, Agent, or Firm—Stewart J. Fried; Jeffrey A. Schwab

[57] ABSTRACT

A sanitary napkin including a stiffening means which because of its resilient properties enables the napkin to lie flat and help it to retain a large degree of its original configuration even after it is subjected to the type of compressive forces that occur during use, is disclosed. The sanitary napkin comprises an absorbent core; a liquid pervious material surrounding the core; a sheet of a liquid impervious material forming a moisture barrier and substantially covering the bottom portion of the napkin, the barrier being positioned between the core and the liquid pervious material; stiffener means located between the core and the liquid impervious material, and a plurality of track adhesive means disposed on the bottom portion of the napkin to secure the napkin to the crotch area of an undergarment, the stiffening means consisting of a material having a high enough level of resiliency and stiffness to resist side compression of the napkin to a sufficient degree to aid in retaining the multi-track adhesive means in place on the undergarment when compressive forces are applied to the napkin during use.

11 Claims, 3 Drawing Figures

SANITARY NAPKIN WITH RESILIENT STIFFENING MEANS

BACKGROUND OF THE DISCLOSURE

I. Field of the Invention

This invention relates to catamenial devices, and more particularly to a sanitary napkin that includes the combination of a plurality of track adhesive means for securing the napkin to the crotch area of an undergarment and a stiffening means which because of its properties helps the napkin to retain a large degree of its original configuration even after it is subjected to the type of compressive forces that occur during use, thereby helping the pad to lie flat and remain in place.

II. Description of the Prior Art

The analysis of clinical data regarding sanitary napkin failures has revealed that poor dimensional stability is often responsible for these failures. Among those failures attributable to poor dimensional stability are; excessive menstrual fluid leakage, side staining, and loss in comfort via pulp bunching, pad shifting, side curling and component separation.

Sanitary napkins have a tendency to collapse along the side portions thereof when they are subject to the type of compressive forces that occur when a napkin is worn. This is especially true once the napkin becomes wet. Once the napkin collapses, there is leakage of the menstrual fluids and subsequent discomfort to the user. The end result is that it becomes necessary for the user to change the napkin quite frequently.

In an attempt to avoid some of the above described problems, it has been suggested to include adhesive fasteners in the form of pressure sensitive adhesive means on the bottom portion of a sanitary napkin, i.e. the side worn away from the body, which permits the napkin to be secured in place in an undergarment, such as a panty. For example, adhesives are illustrated as a fastening means for sanitary napkins and items of related construction in U.S. Pat. Nos. 1,980,958, 2,191,704, 2,273,873, 2,295,016, 3,001,201, 3,063,885, 3,294,091, 3,315,677, 3,454,008, 3,463,154, 3,508,549, 3,672,371, and 3,805,790. Several of these patents illustrate napkins having the adhesive fastening means located toward the longitudinal center of the napkin. This construction, however, has a basic disadvantage of allowing the napkin to leak along its side portions. Furthermore, when the type of napkins as illustrated in these prior art patents are subject to the kind of compressive forces described above, quite often the adhesive is torn away from the undergarment. When this occurs, the sanitary napkin generally moves out of its proper position in the perineal area and either secures itself to an improper position on the undergarment, or as in the case of the dual track adhesive means, it can fold longitudinally thereby causing the adhesive means to stick to itself or other parts of the napkin. In any event the end result is the same, i.e. the sanitary napkin fails and the menstrual fluids flow directly onto the undergarment. This results in a great deal of discomfort to the user and requires frequent changing of the napkin.

For purposes of improving the stability characteristics and/or fluid flow properties of catamenial devices, it has been proposed to incorporate many different types of layers within sanitary napkins. For example, U.S. Pat. No. 811,704 illustrates a layer of a woven fabric reinforcement such as oil silk; U.S. Pat. No. 1,643,615—a waterproof inner liner formed of rubberized cloth, oil cloth, oil silk, or paraffin treated fabric; U.S. Pat. No. 1,843,037—a separator element formed of a lightly waxed crepe cellulose paper; U.S. Pat. No. 1,863,333—compressed layers of crepe paper; U.S. Pat. No. 2,787,271—a combined layer formed of a low absorbent high density material in combination with a woven fabric; U.S. Pat. No. 2,952,259—layers of water repellent tissue, creped tissue or high bulk padding; U.S. Pat. No. 3,424,163—a layer having the combined properties of a liquid spreader and a core strengthener; U.S. Pat. No. 3,570,493—an elastically deformable member extending longitudinally in the tampon; and U.S. Pat. No. Re. 26,939—a layer of creped cellulose wadding. Although the various feminine sanitary products illustrated in these patents employ various kinds of layers which tend to improve the stability and/or fluid flow properties of the products described therein, there still remains a tremendous need for a sanitary napkin which can retain a good deal of its dimensional stability during use.

SUMMARY OF THE INVENTION

It is therefore an object of the present invention to overcome the disadvantages regarding sanitary napkins as stated hereinabove and to provide a sanitary napkin which will exhibit dimensional stability and retain a large degree of its original configuration during use.

It is a further object of this invention to provide a sanitary napkin which will resist the compressive forces that are exerted along the side portions of the napkin when it is worn.

It is a further object of this invention to provide a sanitary napkin which will remain in its original position on the undergarment to which it is attached.

It is a further object of this invention to provide a sanitary napkin which will be comfortable when worn.

It is a further object of this invention to provide a sanitary napkin which will resist fluid leakage and thereby prevent side staining.

It is a further object of the present invention to provide a sanitary napkin having means therein which reduce distortion and keep napkin compression to a minimum thereby increasing overall comfort while maintaining maximum absorbency.

It is still a further object of this invention to provide a sanitary napkin which will decrease the number of failures generally attributable to poor dimensional stability and thereby prevent discomfort and frequent changing of the napkin by the user.

The foregoing objects and others are accomplished in accordance with the present invention by providing a sanitary napkin comprising an absorbent core; a liquid previous material surrounding the core; a sheet of a liquid impervious material forming a moisture barrier and substantially covering the bottom portion of the napkin, the barrier being positioned between the core and the liquid pervious material; a plurality of track adhesive means disposed on the bottom portion of the napkin for securing the napkin to an undergarment; and stiffener means positioned between the core and the liquid impervious material, the stiffening means consisting of a material having a high enough level of resiliency and stiffness to resist side compression to a sufficient degree to aid in retaining the adhesive means in place on the undergarment when compressive forces are applied to the napkin during use.

BRIEF DESCRIPTION OF THE DRAWINGS

For a better understanding of the invention, as well as other objects and further features thereof, reference is made to the following detailed disclosure of this invention taken in conjunction with the accompanying drawings wherein.

DESCRIPTION OF THE PREFERRED EMBODIMENTS

Figure 1:
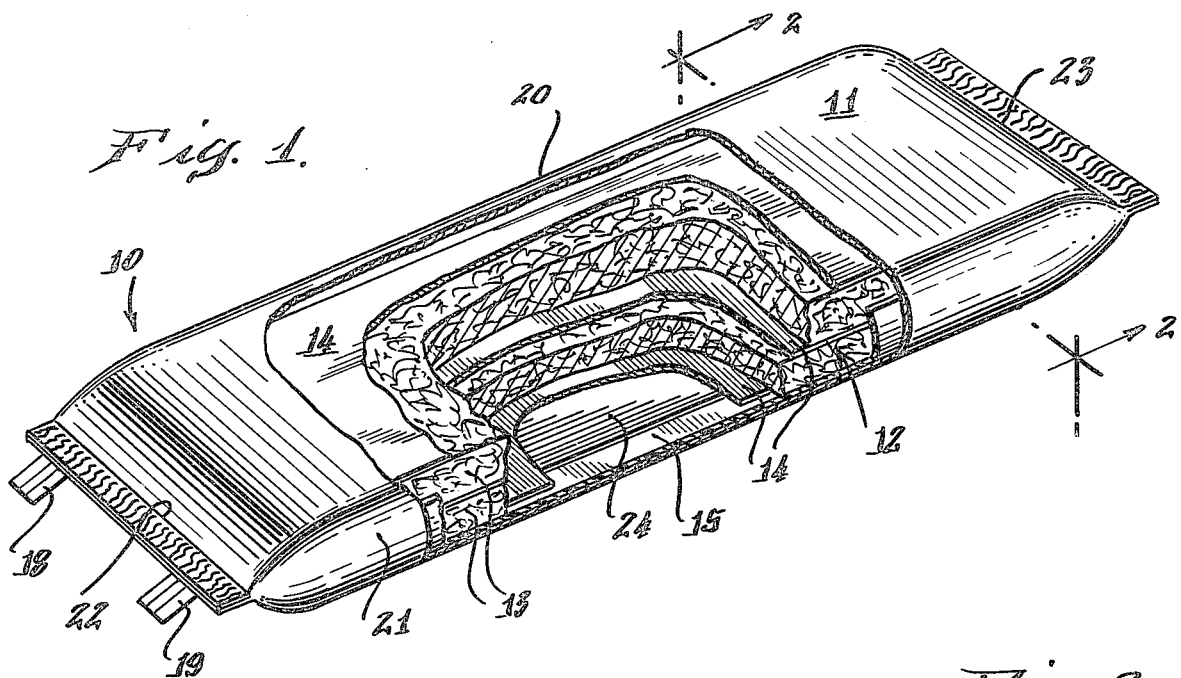
FIG. 1 is a perspective view partly in section illustrating a preferred embodiment of a sanitary napkin in accordance with the present invention.
Figure 2:
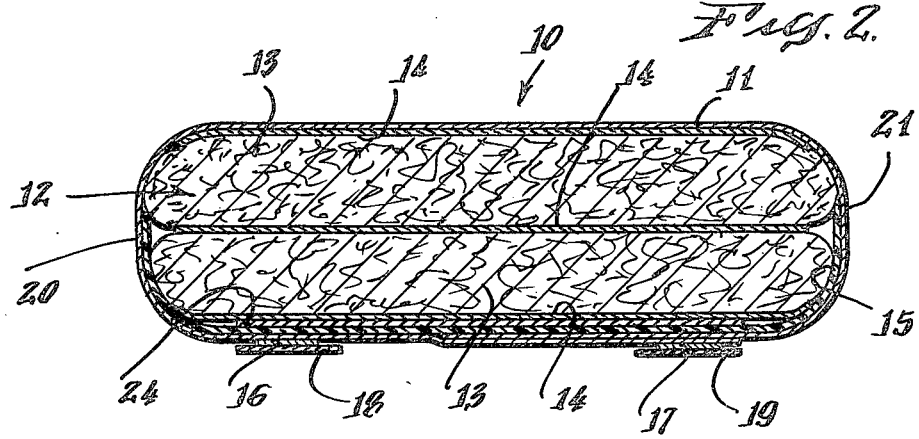
FIG. 2 is a transverse sectional view of the sanitary napkin shown in FIG. 1 taken along line 2—2 thereof.

In FIGS. 1 and 2 there is shown a sanitary napkin 10 in accordance with the features of the present invention. Specifically, the sanitary napkin illustrated is a preferred embodiment which comprises an elongated structure including an outer cover stock material 11 formed of, for example, a non-woven polyester material and, for absorption purposes, pulp core 12. Both the cover stock material and the pulp material could be selected from any of the many conventional materials known in the sanitary napkin art as being used for these purposes. The outer cover stock material may preferably be selected from those fluid-permeable materials which would allow menstrual fluids to flow to the absorbent core, and would also help the napkin to feel dry when it is in use. For example, the material could be formed from a non-woven rayon or polypropylene material. The absorbent core could be a wood pulp fluff, rayon fiber material, cotton, mixtures of rayon and cotton, tissue wadding or any of the many other conventional absorbing materials used in sanitary napkins. The core may contain a material to help increase the absorption properties of the pulp, i.e. a super-absorbent material, such as, for example, a carboxymethyl cellulose (CMC) material made by either of the processes as described in co-pending and commonly assigned Application Ser. No. 906,723, filed May 17, 1978, for "Preparation of Water Insoluble Carboxymethyl Cellulose Absorbents", or Application Ser. No. 906,724, filed May 17, 1978, for "Preparation of Water Insoluble Carboxymethyl Cellulose Absorbents". The core may also contain a deodorant. In the embodiment shown in FIGS. 1 and 2, pulp core 12 is formed of two layers of a pulp fluff material 13 and three separate layers of a carrier tissue paper 14. The tissue paper layers serve a dual purpose, i.e. they facilitate manufacturing the napkin and help to spread the menstrual fluids evenly so as to provide for maximum absorption of these fluids into the napkin.

Located at the bottom portion of the napkin 10, i.e. the portion of the napkin worn away from the body, is a liquid impervious layer 15 which is referred to as a moisture barrier. This layer is preferably formed of a thin layer of plastic of about ½ to about 3 mils in thickness. In accordance with the present invention the material used for the moisture barrier could be selected from any of the conventional materials used for this purpose in sanitary napkins such as, for example, polyethylene, polypropylene, polyvinyl chloride, natural rubber, etc.

In accordance with the features of the present invention, sanitary napkin 10 includes a plurality of track adhesive means located on the bottom portion of the napkin for enabling the user to securely fasten the napkin to the crotch portion of an undergarment. As clearly shown in FIG. 3 one preferred embodiment of a track adhesive means in accordance with this invention comprises a dual track adhesive system including two substantially parallel continuous strips 16 and 17 of a pressure sensitive adhesive material, each of which are covered with overlying release sheets of paper 18 and 19. The release paper is simply peeled away from the adhesive immediately prior to the napkin being used. In addition to being substantially parallel to each other, adhesive strips 16 and 17 are preferably substantially parallel to longitudinal edges 20 and 21 of napkin 10. The track adhesive means in accordance with this invention is not limited to the dual track adhesive system shown in FIGS. 1–3, but could include many other types of track systems. For example, three or more tracks of adhesive could be used. Furthermore, each of the adhesive tracks could be formed of segmented (as compared to continuous) adhesive strips. In addition, the adhesive strips could be formed of different shapes such as, for example, the strips could be rectangular, oval or circular in shape.

As the pressure sensitive adhesive for this invention, any of the polymeric adhesives known to those skilled in the art can be used. Some examples include styrene-butadiene rubber, adhesives marketed under the trade name Buna-N, polyvinyl ethers, polyesters of acrylic acid and polyisobutylene.

Figure 3:
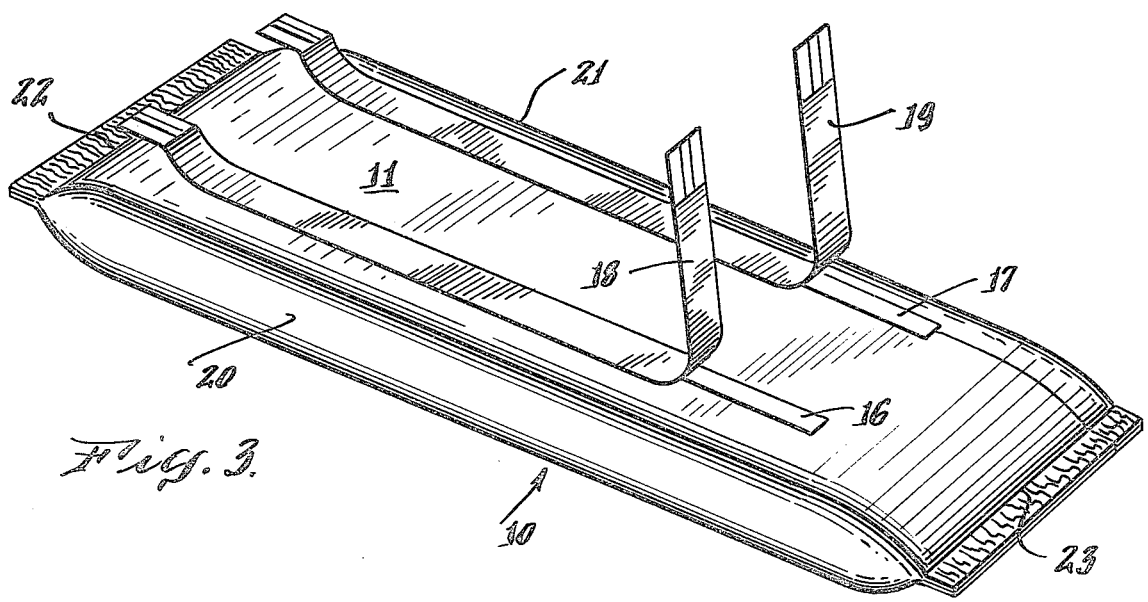
FIG. 3 is a perspective view of a sanitary napkin illustrating a preferred embodiment of the present invention with a dual track adhesive means.

Although as stated above the track adhesive means in accordance with this invention may consist of numerous different shapes and sizes many of which are well known in the art, one preferred embodiment is illustrated in FIGS. 1–3. In these Figures there is illustrated a napkin 10 approximately 9 inches long (7½ inch core length) by 2¾ inch wide including adhesive strips 16 and 17 which are preferably about ⅛ inch in width and which are positioned on the napkin so that they extend longitudinally along the napkin to at least about ½ inch away from each of ends 22 and 23. The adhesive strips are preferably bonded to moisture barrier 15 through cover stock material 11. This can be accomplished by hot extruding adhesive tracks 16 and 17 onto napkin 10.

Positioned between pulp core 12 and moisture barrier 15 is a stiffener means 24 which because of its combined stiffening and resilient properties enables sanitary napkin 10 to lie flat thereby keeping the track adhesive means in place, and helping the napkin to retain a large degree of its original configuration even after it has become wet and has been subject to the type of compressive forces that occur during use. In accordance with the present invention the stiffening means should be formed of a material having a high enough degree of resiliency and stiffness to resist side compression to a sufficient degree so as to aid in retaining the napkin adhesively bonded in place on the undergarment when compressive forces are applied to the napkin during use. In accordance with the preferred embodiment of this invention, stiffener means 24 imparts sufficient stiffness and resiliency to napkin 10, and thereby helps adhesive tracks 16 and 17 to stay apart and remain in place on an undergarment during use. Examples of materials which could be used to form stiffener means 24 in accordance with this invention include spun bonded polyester materials such as, for example, Reemay 2024 sold by E. I.

DuPont Company under the trademark Reemay; fibrous batting materials such as polyester, polyethylene, polypropylene, rayon, nylon, non-absorbent stiffened cotton, and various mixtures of these fibers; foams formed of polyurethane, cellulose, polyethylene, latex, etc.; heavy films formed of polyethylene, vinyl, acetate, latex or rubber; and laminates which could be formed with any combination of the above described spun bonded polyester materials, fibrous batting materials, foams or heavy films, in conjunction with layers of paper, tissues or waddings.

Stiffener means 24 can in accordance with the present invention be formed of any of a variety of materials as described above having a variety of shapes and sizes. In accordance with one preferred embodiment, stiffening means 24 is formed of a substantially rectangular shape of material. To increase the efficiency of the stiffener, and impart greater levels of resiliency and stiffness to the napkin so as to resist side compression sufficiently so that the stiffener coacts with adhesive tracks 16 and 17 to help them remain firmly in place on an undergarment, it has been found that the length of stiffener means 24 may vary from about ½ the length of pulp core 12 to about equal the length of the pulp core. A preferred size for the stiffener means is that its length be substantially the same as the length of core 12 of napkin 10 and its width be at least about ¼ inch narrower than the width of the napkin. When positioning the stiffener within the napkin it is also preferred to allow at least about ⅛ inch spacing between the longitudinal edges of the stiffener and the longitudinal edges of the napkin. With the use of substantially parallel adhesive tracks 16 and 17 it is preferred that the width of the stiffener means be at least equal in dimension to the distance between the two adhesive tracks.

A preferred location for stiffener means 24 in a sanitary napkin in accordance with the present invention is as shown in FIGS. 1 and 2, between core 12 and moisture barrier 15. The close proximity of the stiffener to adhesive tracks 16 and 17 enhances the effect that the stiffener has in coacting with the adhesive tracks and thereby enables them to keep apart and remain in place. Although not required, it is also preferred that stiffener means 24 be bonded within the napkin so as to prevent it from "floating" within the napkin. This can be accomplished by bonding the stiffener to moisture barrier 15 with, for example, a water-based emulsion such as a polyvinylacetate glue or a hot melt adhesive.

EXAMPLE

A group of sanitary napkins having a similar configuration to the sanitary napkin as illustrated in FIGS. 1–3, were prepared. Specifically, napkins were manufactured consisting of an outer layer of a cover stock material formed of a non-woven polyester material which completely surrounded the napkin structure. Located within the polyester cover, and starting from the front portion of the napkin, i.e. that part of the napkin placed against the body, were a first carrier tissue layer (formed of a thin piece of tissue paper), a layer of pulp (formed of a wood pulp fluff), a second carrier tissue layer, a second layer of pulp, followed by a third layer of carrier tissue. Directly beneath the third layer of carrier tissue was the stiffening means formed of Reemay 2024. This material is a spun bonded polyester that is sold by E. I. DuPont Company under the trademark Reemay. Adhesively bonded to the bottom portion of the Reemay stiffener was a moisture barrier formed of a sheet of polyethylene, followed by the outer layer of cover stock material. On the cover stock material were two parallel strips of pressure sensitive adhesive, each of which were adhesively bonded through the cover stock material onto the moisture proof polyethylene layer.

Two types of sanitary napkins were employed in the testing procedure described below. First, napkins having the specific structure as described above were used. Second, napkins as described above without the Reemay 2024 stiffener were used. The napkins without the Reemay stiffener were used for comparative purposes so as to be able to illustrate the effect of this stiffener on the napkins.

Thirty (30) sanitary napkins of each type were tested on an Instron Tensile Tester. The napkins were tested both in a dry and wet condition. Specifically, fifteen (15) napkins of each type were tested dry and fifteen (15) of each type were tested wet. The wet condition was achieved by pouring 15 cc's of water on the center portion of each of the napkins one minute prior to testing them. All of the sanitary napkins tested were weighed prior to testing. The napkins were placed on their sides between the flat plates on the Instron machine and the force necessary to bend the pad 0.95 inches down from their original width was recorded. A bend of ¼ inch was started by hand before placing the napkin between the two plates of the Instron machine. The Instron jaws were placed 2.2 inches apart at the beginning of the test. The test was completed when the jaws were located 1.25 inches apart. The jaw speed was 2.0 inches per minute with a chart recording speed of 10.0 inches per minute. The results of the tests are shown in Table 1.

Table 1

| | Napkin with Stiffener Element | | | | Napkin without Stiffening Element | | | |
|---|---|---|---|---|---|---|---|---|
| | DRY | | WET | | DRY | | WET | |
| Test # | Wt. (gms) | Force (lbs) | Wt. (gms) | Force (lbs) | Wt. (gms) | Force (lbs) | Wt. (gms) | Force (lbs) |
| 1 | 12.56 | 1.2 | 12.74 | .90 | 12.42 | .85 | 12.03 | .60 |
| 2 | 12.79 | 1.1 | 12.91 | .85 | 12.24 | .80 | 12.88 | .75 |
| 3 | 13.07 | 1.1 | 12.52 | .85 | 12.60 | 1.0 | 12.43 | .70 |
| 4 | 12.99 | 1.2 | 12.71 | .80 | 11.91 | .85 | 12.63 | .50 |
| 5 | 13.04 | 1.25 | 12.73 | .80 | 12.08 | .75 | 12.27 | .70 |
| 6 | 12.64 | 1.25 | 13.00 | .95 | 12.37 | .95 | 12.43 | .55 |
| 7 | 12.42 | 1.0 | 12.77 | .90 | 12.00 | .75 | 12.42 | .60 |
| 8 | 12.95 | 1.2 | 12.95 | .85 | 13.12 | 1.1 | 12.03 | .65 |
| 9 | 13.21 | 1.35 | 12.88 | 1.0 | 12.16 | .75 | 11.78 | .50 |
| 10 | 12.30 | 1.05 | 13.07 | .80 | 11.93 | .90 | 11.87 | .50 |
| 11 | 12.79 | 1.05 | 12.97 | .85 | 12.26 | .90 | 11.86 | .50 |
| 12 | 12.95 | 1.15 | 13.21 | 1.05 | 12.90 | 1.05 | 12.51 | .65 |
| 13 | 13.60 | 1.4 | 13.11 | .85 | 12.14 | .75 | 12.68 | .60 |
| 14 | 12.91 | 1.3 | 13.03 | .70 | 12.88 | 1.05 | 12.44 | .60 |
| 15 | 12.09 | 1.0 | 12.13 | .70 | 12.64 | .95 | 12.24 | .60 |
| Avg. | 12.82 | 1.17 | 12.85 | .80 | 12.38 | .89 | 12.30 | .60 |

As seen from the data listed in Table 1, sanitary napkins containing a stiffening means in accordance with this invention show an average 26.4% (dry) and 26.5% (wet) increase in the force necessary to bend the napkins, i.e., an increase in the resistance to compression, as compared to the napkins without the stiffening means. This resistance to compression tends to keep adhesive tracks 16 and 17 apart during use, and helps to keep moisture barrier 15 substantially flat for increased protection. Considering the data listed in Table 1, and taking into consideration such factors as the variables in manufacturing these sanitary napkins on a commercial basis, and the variables in the construction of the napkins, e.g. the amount of the pulp in each napkin, it can be seen that sanitary napkins having the structure in accordance with the teachings of the present invention will show an increase in the napkins' resistance to side compression. This increase in resistance to side compression will help the napkin to lie flat and remain in place during use, and thereby help the adhesive tracks to remain bonded to the undergarment to which they are secured.

We claim:

1. A sanitary napkin comprising an absorbent core; a liquid pervious material surrounding said core; a sheet of a liquid impervious material forming a moisture barrier and substantially covering the bottom portion of said napkin, said barrier being positioned between said core and said liquid pervious material; a plurality of track adhesive means disposed on the bottom portion of said napkin and spaced from the lateral edges thereof for securing said napkin to an undergarment; and stiffener means positioned between said core and said liquid impervious material the width of said stiffener means being at least equal in dimension to the distance between said track adhesive means but less than the width of said napkin, said stiffener means consisting of a material having a high enough level of resiliency and stiffness to resist side compression of said napkin to a sufficient degree to aid in retaining said adhesive means in place on said undergarment when compressive forces are applied to said napkin during use.

2. A sanitary napkin according to claim 1 wherein said stiffener means is adhesively bonded to the moisture barrier.

3. A sanitary napkin according to claim 2 wherein a hot melt adhesive bonds said stiffener means to said moisture barrier.

4. A sanitary napkin according to claim 1 wherein said stiffener means is of a substantially rectangular shape.

5. A sanitary napkin according to claim 1 wherein said stiffener is formed of a spun bonded polyester material.

6. A sanitary napkin according to claim 1 wherein the length of said stiffener means is substantially the same as the length of said core.

7. A sanitary napkin according to claim 1 wherein the width of said stiffener means is at least about $\frac{1}{4}$ inch narrower than the width of said napkin.

8. A sanitary napkin according to claim 1 wherein said adhesive is a pressure sensitive adhesive in the form of two longitudinally extending substantially parallel and continuous tracks, each of said tracks being substantially parallel to the longitudinal edges of said napkin.

9. A sanitary napkin according to claim 8 wherein each of said tracks are about $\frac{1}{8}$ inch in width.

10. A sanitary napkin according to claim 8 wherein the ends of each of said adhesive tracks lie at least about $\frac{1}{2}$ inch from each of the ends of said napkin.

11. A sanitary napkin according to claim 8 wherein said adhesive tracks are bonded to said moisture barrier through said liquid pervious material by hot extruding said strips onto said napkin.

* * * * *